United States Patent
Kim et al.

(10) Patent No.: US 9,249,126 B2
(45) Date of Patent: Feb. 2, 2016

(54) OXETANE-CYCLIC EPOXY COMPOUND, METHOD OF PREPARING THE SAME, AND COMPOSITE SHEET FOR DISPLAY SUBSTRATE INCLUDING THE SAME

(75) Inventors: Young Kwon Kim, Uiwang-si (KR); Sang Keol Lee, Uiwang-si (KR); Tae Ho Kim, Uiwang-si (KR); Woo Jin Lee, Uiwang-si (KR); Sung Kook Kim, Uiwang-si (KR); Hyun Ae Jeon, Ansan-si (KR); Yun Joo Kim, Ansan-si (KR); Sang Yong Tak, Ansan-si (KR); Suk Yeon Park, Ansan-si (KR); Kyung Nam Kang, Ansan-si (KR)

(73) Assignees: CHEIL INDUSTRIES, INC., Gumi-si, Kyeongsangbuk-do (KR); KOREA INSTITUTE OF INDUSTRIAL TECHNOLOGY, Cheonan-si, Chungcheongnam-do (KR)

( * ) Notice: Subject to any disclaimer, the term of this patent is extended or adjusted under 35 U.S.C. 154(b) by 454 days.

(21) Appl. No.: 13/457,741

(22) Filed: Apr. 27, 2012

(65) Prior Publication Data
US 2012/0289108 A1 Nov. 15, 2012

(30) Foreign Application Priority Data
May 12, 2011 (KR) .................. 10-2011-0044645

(51) Int. Cl.
C08J 5/04 (2006.01)
C07D 407/12 (2006.01)
(Continued)

(52) U.S. Cl.
CPC .............. *C07D 407/12* (2013.01); *C08G 65/18* (2013.01); *C08G 65/22* (2013.01); *C08J 5/04* (2013.01); *C08J 5/043* (2013.01);
(Continued)

(58) Field of Classification Search
CPC ................... Y10T 442/2992; Y10T 442/2951; Y10T 428/24994; Y10T 428/2499; C08J 5/04; C08J 5/043; C07D 407/12; C08G 65/18; C08G 65/22
USPC .............. 428/323, 297.4–299.4, 690; 349/88, 349/183
See application file for complete search history.

(56) References Cited

U.S. PATENT DOCUMENTS 3,835,003 A * 9/1974 Schlesinger .................... 522/32
6,166,101 A 12/2000 Takami
(Continued)

FOREIGN PATENT DOCUMENTS

CN 1656156 A 8/2005
EP 1652886 A1 * 5/2006
(Continued)

OTHER PUBLICATIONS

Derwent 2010-N74308; Shichiri, T; JP-2010248387.*
(Continued)

*Primary Examiner* — Jennifer A Steele
(74) *Attorney, Agent, or Firm* — Lee & Morse, P.C.

(57) ABSTRACT

An oxetane-cyclic epoxy compound represented by Formula 1:

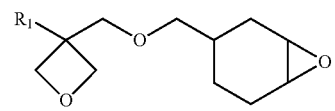

where $R_1$ is hydrogen, a methyl group or an ethyl group.

12 Claims, 2 Drawing Sheets

(51) Int. Cl.
    *C08G 65/18* (2006.01)
    *C08G 65/22* (2006.01)
(52) U.S. Cl.
    CPC ....... *Y10T 428/24994* (2015.04); *Y10T 442/10* (2015.04); *Y10T 442/2951* (2015.04); *Y10T 442/2992* (2015.04)

(56) References Cited

U.S. PATENT DOCUMENTS

| | | | |
|---|---|---|---|
| 6,322,892 | B1 | 11/2001 | Takami |
| 2005/0129877 | A1 | 6/2005 | Akada et al. |
| 2009/0015781 | A1 | 1/2009 | Shimodaira et al. |
| 2010/0009149 | A1* | 1/2010 | Oka et al. .................... 428/220 |

FOREIGN PATENT DOCUMENTS

| | | | | |
|---|---|---|---|---|
| JP | 2003-081958 | A | 3/2003 | |
| JP | 2004-051960 | A | 2/2004 | |
| JP | 2004-233851 | A | 8/2004 | |
| JP | 2005-146258 | A | 6/2005 | |
| JP | 2010248387 | * | 11/2010 | ............ C08G 63/00 |
| KR | 10-2005-0004876 | A | 1/2005 | |

OTHER PUBLICATIONS

Office Action mailed Dec. 24, 2013 in corresponding Korean Patent Application No. 10-2011-0044645.
Office Action mailed Mar. 6, 2014 in corresponding Taiwanese Patent Application No. 101116924.

* cited by examiner

OXETANE-CYCLIC EPOXY COMPOUND, METHOD OF PREPARING THE SAME, AND COMPOSITE SHEET FOR DISPLAY SUBSTRATE INCLUDING THE SAME

BACKGROUND

1. Field

Embodiments relate to an oxetane-cyclic epoxy compound, a method of preparing the same, and a composite sheet for display substrate including the same.

2. Description of the Related Art

Glass having excellent heat resistance and transparency, and a low coefficient of linear expansion is widely used as substrates for liquid crystal displays (LCDs) or organic electroluminescent (EL) displays, color filter substrates, solar cell substrates, or the like. Recently, as substrate materials for displays are required to have small size, slimness, light weight, impact resistance and flexibility, plastic materials are receiving attention as a substitute for a glass substrate.

SUMMARY

Embodiments are directed to an oxetane-cyclic epoxy compound represented by Formula 1:

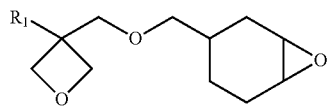

where $R_1$ is hydrogen, a methyl group or an ethyl group.

Embodiments are also directed to a method of preparing an oxetane-cyclic epoxy compound represented by Formula 1, including preparing cyclohexenyl oxetane ether by reacting cyclohexenyl methanol and an oxetane compound represented by Formula 2, and oxidizing the cyclohexenyl oxetane ether:

[Formula 1]

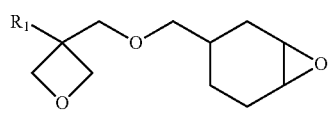

where $R_1$ in Formula 1 is hydrogen, a methyl group or an ethyl group; and

[Formula 2]

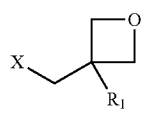

where $R_1$ in Formula 2 is a methyl group or an ethyl group, and X is Cl, Br, I, $CH_3C_6H_4SO_3$ or $CF_3SO_3$.

Embodiments are also directed to a composite sheet formed using the oxetane-cyclic epoxy compound according to an embodiment as a binder.

The composite sheet may further include glass fillers.

The composite sheet may include about 60 to about 300 parts by weight of the glass fillers, based on 100 parts by weight of the binder.

The glass fillers may include at least one selected from the group of glass fiber, glass fiber cloth, glass fabric, unwoven glass cloth, glass mesh, glass beads, glass powder, and glass flakes.

The binder may be formed using the oxetane-cyclic epoxy compound and a cation polymerizable compound.

The cation polymerizable compound may include at least one selected from the group of an epoxy group-containing compound, an oxetane group-containing compound, a vinyl ether group-containing compound, and a caprolactone group-containing compound.

The binder may have a difference in index of refraction of about 0.01 or less from the glass filler.

The binder may be formed using the oxetane-cyclic epoxy compound and a cationic initiator.

The composite sheet may have a glass transition temperature of about 200° C. or higher.

Embodiments are also directed to a display substrate including the composite sheet according to an embodiment.

The substrate may have a coefficient of thermal expansion of about 30 ppm/° C. or less, measured by a thermomechanical analyzer (TMA) at 5° C./min from 30 to 250° C.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
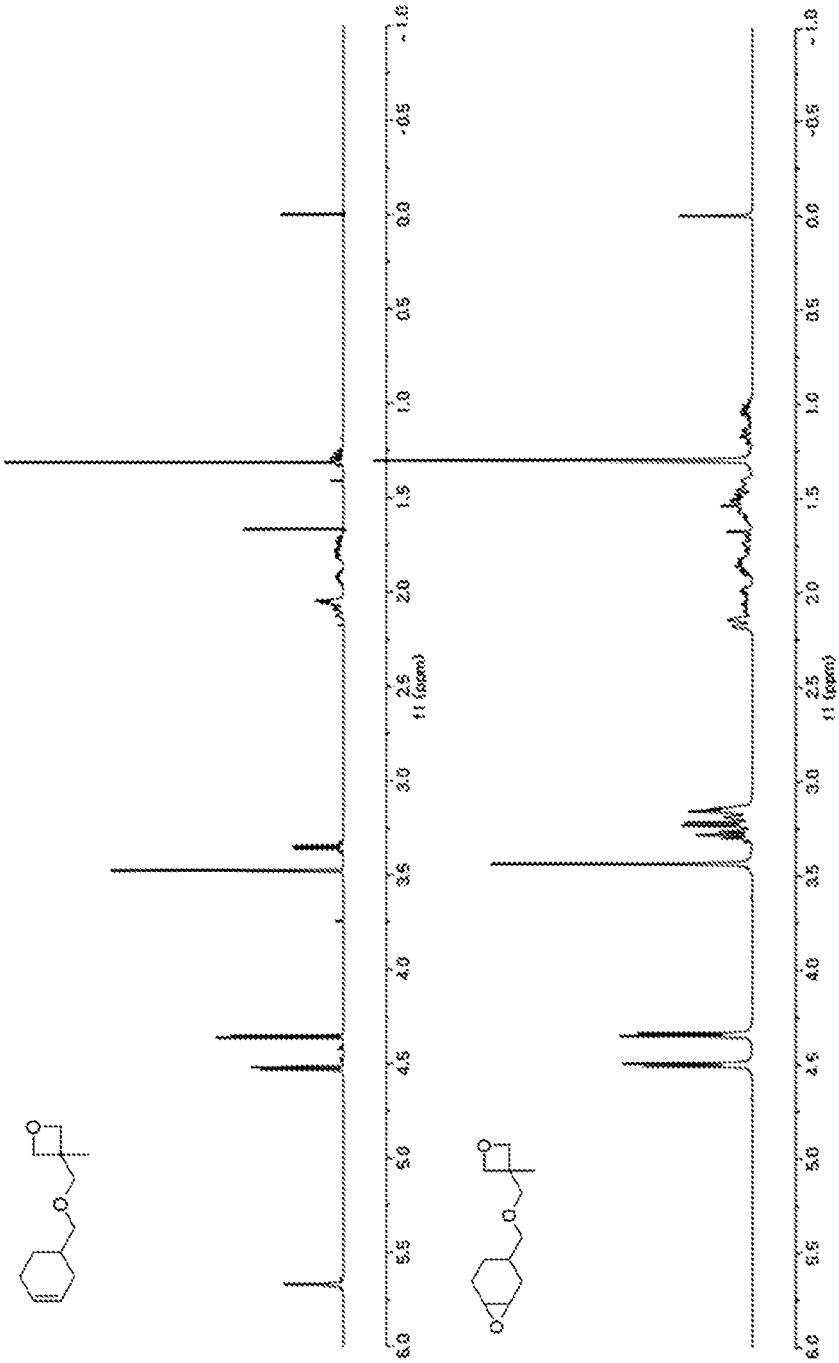
FIG. 1 illustrates NMR data of oxetane compounds prepared in Preparative Example 1 according to an embodiment.

Korean Patent Application No. 10-2011-0044645, filed on May 12, 2011, in the Korean Intellectual Property Office, and entitled: "Novel Oxetane Compound, Method of Preparing the Same, and Composite Sheet for Display Substrate Including the Same," is incorporated by reference herein in its entirety.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

An embodiment is directed to an oxetane-cyclic epoxy compound represented by Formula 1:

[Formula 1]

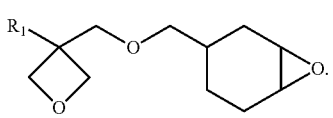

In an embodiment, $R_1$ in Formula 1 may be hydrogen, a methyl group or an ethyl group. In another embodiment, $R_1$ may be hydrogen.

In an embodiment, the oxetane-cyclic epoxy compound may be prepared by (1) preparing a cyclohexenyl oxetane ether through reaction of cyclohexenyl methanol and an oxetane compound represented by Formula 2 (see below); and then (2) oxidizing the cyclohexenyl oxetane ether.

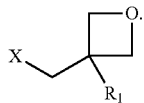

[Formula 2]

In an embodiment $R_1$ in Formula 2 may be a methyl group or an ethyl group, and X may be a leaving group such as Cl, Br, I, $CH_3C_6H_4SO_3$, or $CF_3SO_3$ ("triflate"). In another embodiment, $R_1$ may be hydrogen.

The oxetane-cyclic epoxy compound may be prepared by the following Reactions 1 and 2:

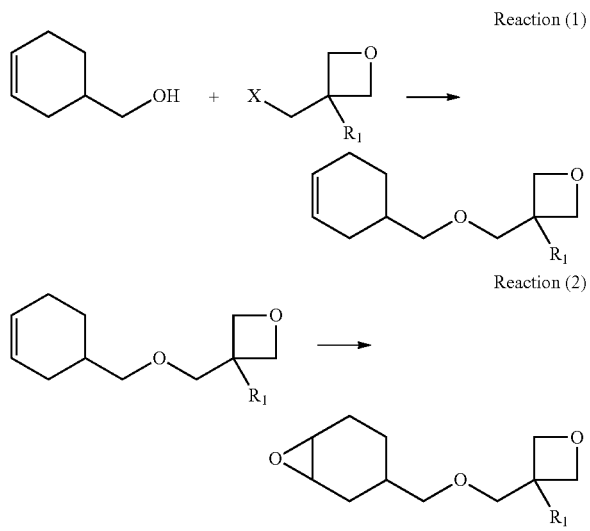

Reaction (1) of synthesizing the cyclohexenyl oxetane ether may be carried out at, e.g., about −10 to about 100° C. The reaction may be carried out in the presence of a strong base. In the reaction of cyclohexenyl methanol and the oxetane compound represented by Formula 2, the oxetane compound may be present at an equivalent ratio of about 0.5 to about 4, preferably about 0.8 to about 3, to the cyclohexenyl methanol.

Reaction (2) of oxidizing the cyclohexenyl oxetane ether may be carried out by adding an oxidant. Suitable oxidants may include, e.g., meta-chloroperoxybenzoic acid (m-CPBA), peroxybenzoic acid, etc. The oxidation may be carried out in a halogen-containing solvent. The reaction temperature may be, e.g., about 20 to about 100° C.

The oxetane-cyclic epoxy compound according to an embodiment may be suitably used as a binder of a composite sheet for a display substrate. A composite sheet according an embodiment includes a binder and glass fillers, the binder being formed using the oxetane-cyclic epoxy compound according to an embodiment. The binder may be formed using a resin that includes the oxetane-cyclic epoxy compound represented by Formula 1.

The oxetane-cyclic epoxy compound in Formula 1 has an asymmetric structure of a single oxetane group and cyclic epoxy at a terminal, and has a low molecular weight. Thus, the concentration of reactive functional groups may be high. Accordingly, heat resistance in the resultant composite sheet may be improved, and an inflection point of a glass transition temperature determination may not appear at temperatures of about 250° C. or less, due to the high crosslinking density of the cured resin. In addition, the cyclohexane group remains after curing the oxetane-cyclic epoxy compound having the above structure as a binder, and thus the binder may exhibit excellent mechanical properties and optical properties, and viscosity may decrease, thereby providing excellent processibility for the preparation of glass filler composite.

In an embodiment, the binder may be formed using the oxetane-cyclic epoxy compound represented by Formula 1 alone. In an embodiment, the binder may be formed using a cationic polymerizable compound together with the oxetane-cyclic epoxy compound represented by Formula 1.

The cationic polymerizable compound may include, e.g., epoxy group-containing compounds, oxetane group-containing compounds, vinyl ether group-containing compounds, caprolactone group-containing compounds, etc. For example, the cationic polymerizable compound may include one or more compounds such as a glycidyl epoxy resin (e.g., a bisphenol A epoxy resin, a bisphenol F epoxy resin, a bisphenol S epoxy resin, etc.), 2-hydroxyethyl vinyl ether, diethylene glycol monovinyl ether, 4-hydroxybutyl vinyl ether, diethylene glycol vinyl ether, triethylene glycol divinyl ether, cyclohexanedimethanol divinyl ether, cyclohexanedimethanol monovinyl ether, tricyclodecane vinyl ether, cyclohexyl vinyl ether, methoxyethyl vinyl ether, ethoxyethyl vinyl ether, and tetravinyl ether of pentaerythritol.

The cationic polymerizable compound may be used in an amount of about 99 wt % or less, for example, about 0.01 to about 95 wt %, in the entire binder. In an embodiment, the cationic polymerizable compound may be present in an amount of about 1 to about 75 wt % or less, preferably about 3 to about 70 wt %, and more preferably about 5 to about 65 wt %, in the entire binder. In an embodiment, the cationic polymerizable compound may be present in an amount of about 5, 10, 15, 20, 25, 30, 35, 40 45, 50, 55, 60 or 65 wt % in the entire binder. Within this range, the index of refraction of the binder may be matched with that of the glass filler, thereby producing a composite sheet having excellent light transmittance.

In an embodiment, a weight ratio of the oxetane-cyclic epoxy compound represented by Formula 1 to the cationic polymerizable compound may be about 1:0.05 to about 1:4. Within this range, excellent heat resistance may be exhibited and a light transmitting film may be manufactured by matching the index of refraction of the binder with that of the glass filler. In an embodiment, a weight ratio of the oxetane-cyclic epoxy compound to the cation polymerizable compound may be about 1:1.0 to about 3.5, preferably about 1:1.5 to about 3.

In an embodiment, the binder may have a difference in index of refraction of about 0.01 or less from the glass fillers. If glass fiber has a diameter of 100 nm or greater, light transmittance may deteriorate due to light scattering on a glass fiber interface. In order to prevent deterioration in light transmittance, a difference in index of refraction between the glass fiber and the binder may be about 0.01 or less, preferably about 0.0001 to about 0.007, and more preferably about 0.0005 to about 0.005. Within this range, excellent transparency and light transmittance may be obtained.

In an embodiment, the binder may have a glass transition temperature of about 150° C. or higher, preferably about 200° C. or higher, and more preferably have no glass transition temperature (referred to herein as a Tg-less system). Within this range, the binder may provide excellent mechanical strength without a drastic change in modulus.

The binder may have a light transmittance of about 80 to about 99%, preferably about 85 to about 95%. Within this range, excellent transparency and display quality may be obtained.

The binder may have a coefficient of thermal expansion (CTE) of about 20 ppm/° C. or less, preferably about 0.01 to about 15 ppm/° C., and more preferably about 0.01 to about 13 ppm/° C. Within this range, suitable heat resistance for a substrate may be secured.

The reactive functional group of Formula 1 applied to the binder may have an equivalent weight of about 120 g/eq or less, preferably about 110 g/eq or less, and more preferably about 1 to about 108 g/eq. Due to a low molecular weight/equivalent weight of the reactive functional group, the cured resin may have a high crosslinking density.

The glass fillers used in the composite sheet according to an embodiment may include, e.g., glass fiber, glass fiber cloth, glass fabric, unwoven glass cloth, glass mesh, glass beads, glass powder, glass flakes, etc. These glass fillers may be used alone or in combination thereof. In an implementation, glass fillers in a sheet form, such as glass fiber cloth, glass fabric, unwoven glass cloth, and glass mesh, etc., may be used.

The glass fillers may be present in an amount of about 60 to about 300 parts by weight based on 100 parts by weight of the binder. Within this range, a CTE suitable for a substrate may be provided. In an implementation, the glass fillers may be present in an amount of about 67 to about 250 parts by weight based on 100 parts by weight of the binder.

In an embodiment, the binder for the composite sheet may be formed using a cationic initiator. The cationic initiator may include curing catalysts of, e.g., one or more of onium cations and aluminum chelate cations. For example, the cationic initiator may include one or more of an aromatic sulfonium salt, an aromatic iodonium salt, an ammonium salt, an aluminum chelate, a boron trifluoride amine complex, etc. The aromatic sulfonium salt may include, e.g., hexafluoroantimonate salt; the aluminum chelate may include one or more of, e.g., aluminum ethylacetoacetate diisopropylate and aluminum tris (ethylacetoacetate); and the boron trifluoride amine complex may include one or more of, e.g., a boron trifluoride monoethylamine complex, a boron trifluoride imidazole complex, and a boron trifluoride piperidine complex. These cationic initiators may be used alone or in combination thereof. The cationic initiator may be present in an amount of about 0.01 to about 10 parts by weight, preferably about 0.05 to about 5 parts by weight, based on 100 parts by weight of the binder. Within this range, curing reaction of the composite composition may be sufficiently carried out.

The composite sheet according to an embodiment may also include one or more of, e.g., antioxidants, UV absorbers, dyes, pigments, coupling agents, other inorganic fillers, and the like.

The composite sheet may be manufactured in a sheet form by impregnating binder components with a glass filler and crosslinking. The sheet may have a thickness of about 50 to about 200 μm, preferably about 70 to about 150 μm.

Figure 3:
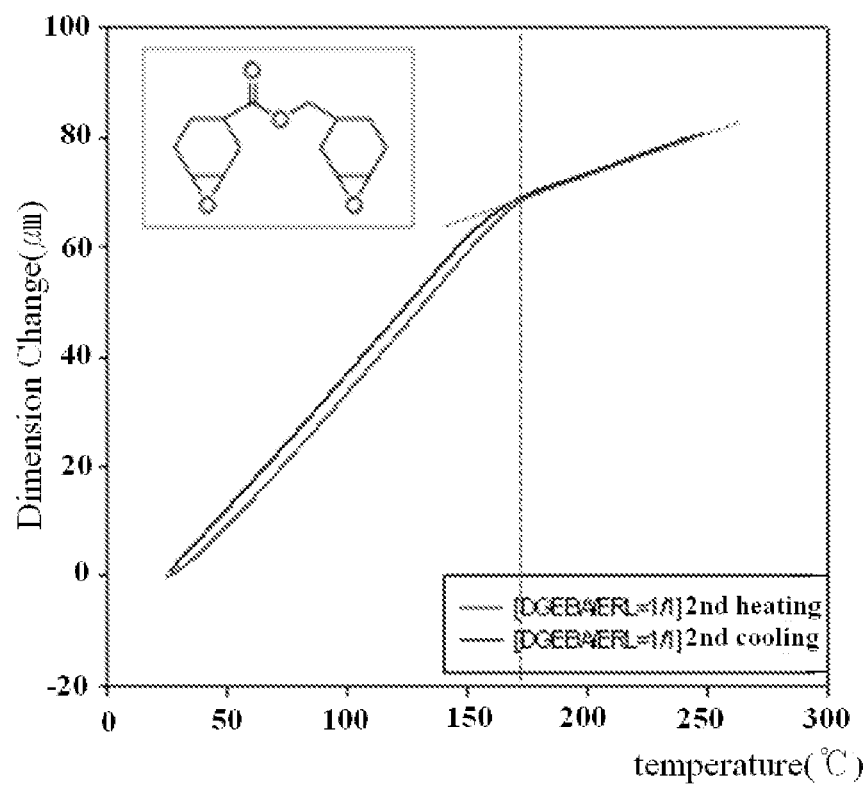
FIG. 3 illustrates a TMA graph of a composite sheet prepared in Comparative Example 1.

In an embodiment, the composite sheet may have a glass transition temperature of about 150° C. or higher, preferably about 200° C. or higher. In another embodiment, the composite sheet may have no glass transition temperature (Tg-less) at about 250° C. or less. Here, the term "no glass transition temperature (Tg-less)" means that an inflection point does not appear in a plot of temperature vs. dimension change (μm) measured using a thermomechanical analyzer (TMA). In detail, as shown in FIG. 3, a composite sheet employing a general binder has an inflection point at 170° C. in the TMA data. However, the composite sheet having no glass transition temperature (Tg-less) according to an embodiment does not have an inflection point in the same range.

As described above, the composite sheet according to an embodiment may not have an inflection point (Tg-less) in a temperature range used in one or more manufacturing processes. Thus, excellent thermal resistance may be secured without damage to flexibility. Further, when the oxetane-cyclic epoxy compound is used as a binder, low viscosity may be maintained since the oxetane-cyclic epoxy compound is not aromatic and has a low molecular weight, thereby providing wettability in preparation of a composite.

The composite sheet according to an embodiment may be used for, e.g., displays or light emitting devices, such as a liquid crystal display (LCD) substrates, color filter substrates, organic electroluminescent (EL) display substrates, solar cell substrates, and touch screen panel substrates.

When the composite sheet according to an embodiment is used for a display substrate, a hard coating layer and a gas barrier layer may be further included on at least one side thereof. The hard coating layer and the gas barrier layer may be formed according to a general process.

The substrate according to an embodiment may have a coefficient of thermal expansion ($\alpha_1$) of about 30 ppm/° C. or less, preferably about 20 ppm/° C. or less, and more preferably about 0.01 to about 15 ppm/° C., measured by a TMA at 5° C./min from 30 to 250° C. For example, when the content of binder is about 60 wt % in the entire composite sheet, the coefficient of thermal expansion ($\alpha_1$) may be about 20 to 25 ppm/° C. In another embodiment, when the content of binder is about 40 wt % in the entire composite sheet, the coefficient of thermal expansion ($\alpha_1$) may be about 10 to about 15 ppm/° C. In another embodiment, when the content of binder is about 30 wt % or less in the entire composite sheet, the coefficient of thermal expansion ($\alpha_1$) may be less than about 10 ppm/° C.

The substrate may have a light transmittance of about 80% or more, preferably about 85% or more, and more preferably about 86% or more at a wavelength of 550 nm. In an embodiment, the substrate may have a light transmittance of about 87 to 99%.

The following Examples and Comparative Examples are provided in order to set forth particular details of one or more embodiments. However, it will be understood that the embodiments are not limited to the particular details described. Further, the Comparative Examples are set forth to highlight certain characteristics of certain embodiments, and are not to be construed as either limiting the scope of the invention as exemplified in the Examples or as necessarily being outside the scope of the invention in every respect.

EXAMPLES

Preparative Example 1

Synthesis of Oxetane-Cyclic Epoxy

NaH (6.4 g) and 150 ml of DMF were put in a 500 ml flask and stirred. After temperature was lowered using an ice bath, cyclohexenyl methanol (15 g) was slowly added to the mixture and stirred at room temperature for 15 minutes. After the temperature was lowered using the ice bath again, an oxetane chloride (14.5 g) was slowly added to the mixture for 10 minutes and stirred at room temperature for 2 hours. After completion of reaction, $H_2O$ was slowly added to the product to remove the activity of remaining NaH, followed by working-up with ether/$H_2O$ three times. $MgSO_4$ was put into an organic layer, followed by filtering and elimination of the solvent using an evaporator, thereby obtaining colorless liquid cyclohexenyl oxetane ether at a yield of 93%.

$^1$H NMR (500 MHz, CDCl$_3$): δ=1.25-1.30 (m, 1H), 1.31 (s, 3H), 1.71-1.83 (m, 2H), 1.88-1.97 (m, 1H), 2.04-2.14 (m, 3H), 3.35 (dd, 2H, 5 Hz, 2 Hz), 3.48 (s, 2H), 4.36 (d, 2H, 5.5 Hz), 4.53 (d, 2H, 6 Hz), 5.66-5.67 (m, 2H)

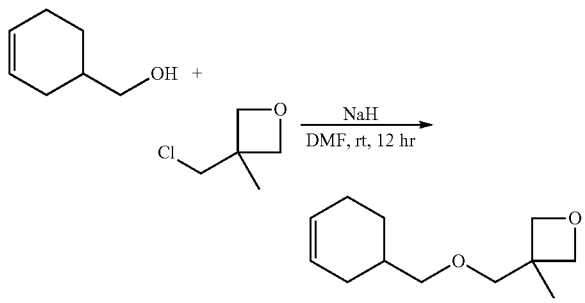

The obtained cyclohexenyl oxetane ether (20 g) was stirred in 50 ml of methylene chloride (MC) in a 250 ml flask at room temperature for 5 minutes. A solution obtained by dissolving 77% m-CPBA (27.4 g) in 100 ml of methylene chloride was slowly added to the mixture for 30 minutes, and then heated and refluxed for 3 hours. After completion of reaction, temperature was lowered to room temperature, and the product was then filtered and an organic layer was worked up with a K$_2$CO$_3$ solution. MgSO$_4$ was put into the organic layer, followed by filtering and removal of the solvent using an evaporator, thereby obtaining oxetane-cyclic epoxy at a yield of 70%. The obtained oxetane-cyclic epoxy was a colorless liquid, and an NMR result thereof is shown in FIG. 1.

$^1$H NMR (500 MHz, CDCl$_3$): δ=0.98-1.21 (m, 1H), 1.30 (s, 3H), 1.41-1.90 (m, 4H), 1.98-2.10 (m, 1H), 2.14-2.18 (m, 1H), 3.15-3.31 (m, 4H), 3.44 (s, 2H), 4.35 (dd, 2H, 4.5 Hz, 1.5 Hz), 4.51 (d, 2H, 5.5 Hz)

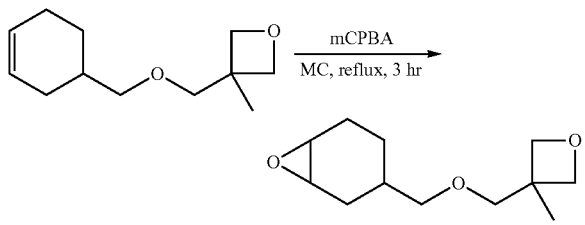

Example 1

Figure 2:
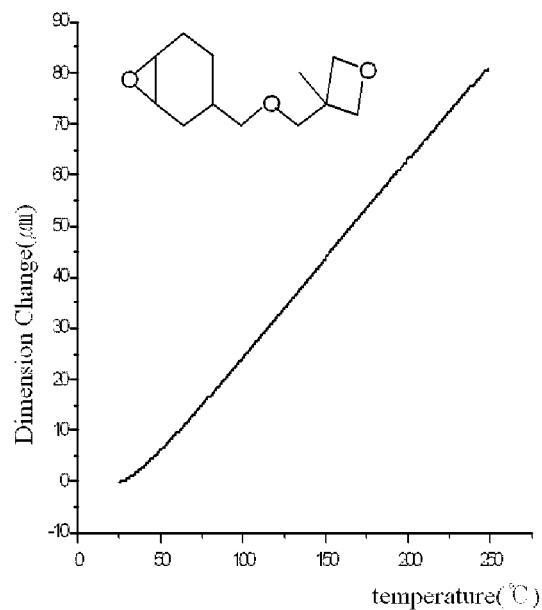
FIG. 2 illustrates a TMA graph of a composite sheet prepared in Example 1.

Preparation of Composite Sheet 4.9 g of the oxetane-cyclic epoxy synthesized in Preparative Example 1, 5.1 g of diglycidyl ether of bisphenol A and 0.2 g of triarylsulfonium hexafluoroantimonate salt were thoroughly mixed. The mixture was impregnated with 10 g of E-glass glass fiber (product name: 3313, Nittobo Co., Ltd.), after which the product was placed between release-treated glass substrates and UV light was irradiated to both sides of the substrates for 2 minutes, thereby producing a transparent composite sheet (resin content: 50 wt %) having a binder content of 50 wt %. A TMA graph is illustrated in FIG. 2.

Comparative Example 1

A transparent composite sheet was manufactured in the same manner as in Example 1 except that monofunctional oxetane represented by Formula 3, (3-methyloxetan-3-yl)methanol, was used instead of the oxetane-cyclic epoxy synthesized in Preparative Example 1. The resultant transparent composite sheet had too low crosslinking density, making it difficult to form a film.

[Formula 3]

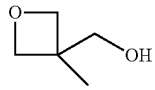

Comparative Example 2

A transparent composite sheet was manufactured in the same manner as in Example 1 except that difunctional epoxy represented by Formula 4, 7-oxa-bicyclo[4.1.0]heptan-3-yl-methyl-7-oxa-bicyclo[4.1.0]heptane-3-carboxylate, was used instead of the oxetane-cyclic epoxy synthesized in Preparative Example 1. A TMA graph is illustrated in FIG. 3.

[Formula 4]

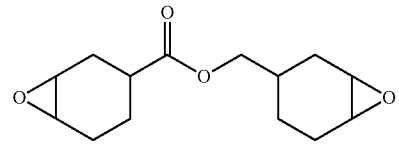

The transparent composite sheets prepared in Example 1 and Comparative Examples 1 and 2 were evaluated as to physical properties as follows.

(1) Light Transmittance

Light transmittance (%) at a wavelength of 550 nm was evaluated using a UV-Vis spectrometer.

(2) Coefficient of Thermal Expansion (CTE) and Glass Transition Temperature (Tg)

After a variation of dimensional change with temperature was measured using a thermo-mechanical analyzer (TMA) (Expansion mode, Force 0.05N), the CTE (ppm/° C.) and the glass transition temperature (° C.) of a specimen were obtained from a curve indicating a change in specimen length with temperature.

TABLE 1

|  | Light transmittance @ 550 nm | CTE (ppm/° C.) @ 30~250° C. | Tg (° C.) | Molecular weight/ equivalent weight of reactive functional groups (g/eq) |
| --- | --- | --- | --- | --- |
| Example 1 | 87% | 12 | >250° C. (Tg-less) | 106 |
| Comparative Example 1 | Did not form composite film | — | — | 102 |
| Comparative Example 2 | 88% | 14 @ 30~170° C. | 170° C. | 126 |

As can be seen from Table 1, the composite sheet according to Example 1 maintained initial strength and physical properties at a decomposition temperature of a polymer (350° C. or higher) without glass transition. However, the composite sheet according to Comparative Example 1 had too low curing density, such that a film was not formed. The composite sheet according to Comparative Example 2 had an increasing CTE and a glass transition temperature of 170° C. Therefore, it can be seen that the composite sheet including the oxetane-epoxy compound as a binder according to an embodiment may provide excellent heat resistance.

By way of summation and review, materials such as polyethylene terephthalate (PET), polyethersulfone (PES), polyethylene naphthalate (PEN), polyarylate (PAR), polycarbonate (PC) and polyimide (PI) have been used as plastic substrates. However, these materials have a considerably high coefficient of thermal expansion, and thus may cause bending of products or breaking of wires. Although a PI resin has a somewhat lower coefficient of thermal expansion, it may not be well suited to a substrate material due to its remarkably low transparency, high birefringence, and hygroscopic properties.

In view of the above, a transparent composite optical sheet may be prepared using ester group-containing alicyclic epoxy resins, bisphenol A epoxy resins, an acid anhydride curing agent, a catalyst, and glass fiber cloth. Also, a transparent composite optical sheet may be formed of alicyclic epoxy resins containing an ester group, epoxy resins having a dicyclopentadiene structure, an acid anhydride curing agent and glass fiber cloth. Also, a transparent substrate may be formed of bisphenol A epoxy resins, bisphenol A novolac epoxy resins, an acid anhydride curing agent, and glass fiber cloth. However, such composite sheets may have a Tg in the range of 145 to 160° C., which is lower than a process temperature, thereby exhibiting reduced heat resistance and deteriorated processibility.

In order to increase the Tg of a composite sheet, a benzene ring or fullerene structure may be introduced into a binder structure. However, when a benzene ring or fullerene structure is introduced, a resultant sheet may have reduced flexibility and become rigid, and may thus not be well suited to a flexible substrate. Further, the sheet may have increased viscosity, thereby causing deterioration in solubility and wettability, and may become brittle.

As described above, embodiments may provide an oxetane compound, a method of preparing the same, and a composite sheet which includes the oxetane compound. Embodiments may provide materials that exhibit excellent flexibility, transparency, and heat resistance, good resistance to impact, elongation, and bending, a low coefficient of thermal expansion, excellent light transmittance and low viscosity, and may thus provide excellent processibility and wettability for the preparation of a glass filler composite, to have no glass transition in the temperature range of processes, providing excellent heat resistance, and to adjust a curing rate. Further, embodiments may provide a display substrate which uses the composite sheet, thus being small-sized, slim, light, and inexpensive. A composite sheet that employs an oxetane-cyclic epoxy compound according to an embodiment as a binder may exhibit excellent heat resistance, optical properties, crack resistance, mechanical properties, and processibility, while having superior flexibility.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A composite sheet, comprising:
 a binder, the binder being formed using an oxetane-cyclic epoxy compound represented by Formula 1,

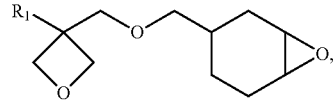

wherein, in Formula 1, $R_1$ is hydrogen, a methyl group, or an ethyl group; and
 glass fillers,
 wherein the oxetane and epoxy reactive functional groups of Formula 1 have an equivalent weight of about 120 g/eq or less.

2. The composite sheet as claimed in claim 1, comprising: about 60 to about 300 parts by weight of the glass fillers, based on 100 parts by weight of the binder.

3. The composite sheet as claimed in claim 1, wherein the glass fillers comprise at least one selected from the group of glass fiber, glass fiber cloth, glass fabric, unwoven glass cloth, glass mesh, glass beads, glass powder, and glass flakes.

4. The composite sheet as claimed in claim 1, wherein the binder is formed using the oxetane-cyclic epoxy compound and a cation polymerizable compound.

5. The composite sheet as claimed in claim 4, wherein the cation polymerizable compound comprises at least one selected from the group of an epoxy group-containing compound, an oxetane group-containing compound, a vinyl ether group-containing compound, and a caprolactone group-containing compound.

6. The composite sheet as claimed in claim 4, wherein the binder has a difference in index of refraction of about 0.01 or less from the glass filler.

7. The composite sheet as claimed in claim 1, wherein the binder is formed using the oxetane-cyclic epoxy compound and a cationic initiator.

8. The composite sheet as claimed in claim 1, wherein the composite sheet has a glass transition temperature of about 200° C. or higher.

9. A display substrate comprising the composite sheet as claimed in claim 1.

10. The display substrate as claimed in claim 9, wherein the substrate has a coefficient of thermal expansion of about 30 ppm/° C. or less, measured by a thermomechanical analyzer (TMA) at 5° C./min from 30 to 250° C.

11. The composite sheet as claimed in claim 4, wherein a weight ratio of the oxetane-cyclic epoxy compound to the cation polymerizable compound in the binder is about 1:1.5 to about 1:3.

12. A composite sheet, comprising:
 a binder, the binder being formed using a cation polymerizable compound, a cationic initiator, and an oxetane-cyclic epoxy compound represented by Formula 1,

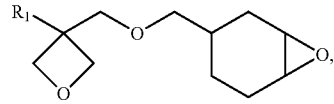

wherein, in Formula 1, $R_1$ is hydrogen, a methyl group, or an ethyl group; and glass fillers, wherein:

the content of the binder in the composite sheet is about 60 wt % or less, and the composite sheet has no glass transition temperature at about 250° C. or less.

* * * * *